(12) United States Patent
Drake et al.

(10) Patent No.: US 11,027,124 B2
(45) Date of Patent: Jun. 8, 2021

(54) INTERVENTIONAL MEDICAL SYSTEMS AND RETRIEVAL TOOLS THEREOF

(71) Applicant: Medtronic, Inc., Minneapolis, MN (US)

(72) Inventors: Ronald A Drake, St. Louis Park, MN (US); Keith D Anderson, Minneapolis, MN (US); Kenneth C Gardeski, Plymouth, MN (US); Dina L Williams, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 361 days.

(21) Appl. No.: 15/264,375

(22) Filed: Sep. 13, 2016

(65) Prior Publication Data

US 2018/0071518 A1 Mar. 15, 2018

(51) Int. Cl.
*A61N 1/05* (2006.01)
*A61B 17/00* (2006.01)
(Continued)

(52) U.S. Cl.
CPC ........ *A61N 1/057* (2013.01); *A61B 17/00234* (2013.01); *A61B 17/221* (2013.01);
(Continued)

(58) Field of Classification Search
CPC ........ A61B 17/221; A61B 2017/00358; A61B 2017/2212; A61B 17/50;
(Continued)

(56) References Cited

U.S. PATENT DOCUMENTS 5,171,233 A 12/1992 Amplatz et al.
5,279,539 A 1/1994 Bohan et al.
(Continued)

FOREIGN PATENT DOCUMENTS

CN 202020521 U 11/2011
CN 202821516 U 3/2013
(Continued)

OTHER PUBLICATIONS

U.S. Appl. No. 14/926,827 entitled "Interventional Medical Systems, Associated Assemblies and Methods".
(Continued)

*Primary Examiner* — Majid Jamialahmadi
(74) *Attorney, Agent, or Firm* — Shumaker & Sieffert, P.A.

(57) ABSTRACT

A tool operable with a catheter in an interventional medical system retrieves a medical device from an implant site, wherein the device includes an attachment feature that forms an annular recess to be engaged by a lasso of the tool for snaring the device, and a distal-most sidewall of the catheter defines a receptacle into which the snared device is retrieved. A guide of the tool includes a sidewall defining a lumen in which the lasso extends for deployment out from a distal opening thereof, to snare and retrieve the implanted device. The sidewall establishes a radial offset between the guide lumen distal opening and the distal-most sidewall of the catheter, when the guide lumen distal opening and a distal opening of the receptacle are located in close proximity to one another, which radial offset is greater than a length of the annular recess formed by the device attachment feature.

16 Claims, 8 Drawing Sheets

(51) Int. Cl.
*A61B 17/50* (2006.01)
*A61N 1/372* (2006.01)
*A61B 17/221* (2006.01)
*A61N 1/375* (2006.01)
*A61N 1/362* (2006.01)

(52) U.S. Cl.
CPC .............. *A61B 17/50* (2013.01); *A61N 1/372* (2013.01); *A61N 1/3756* (2013.01); *A61B 2017/00243* (2013.01); *A61B 2017/00358* (2013.01); *A61N 1/362* (2013.01); *A61N 1/37205* (2013.01); *A61N 1/37512* (2017.08); *A61N 1/37518* (2017.08); *A61N 2001/0578* (2013.01)

(58) Field of Classification Search
CPC .. A61B 2017/22035; A61B 2017/2215; A61B 2017/2217; A61B 2017/000243; A61N 2001/0578; A61N 1/057; A61N 1/37205
See application file for complete search history.

(56) References Cited

U.S. PATENT DOCUMENTS

| | | | | |
|---|---|---|---|---|
| 5,387,219 | A | * | 2/1995 | Rappe ................ A61B 17/1214 606/1 |
| 5,522,819 | A | * | 6/1996 | Graves ................ A61B 17/221 606/110 |
| 5,562,678 | A | | 10/1996 | Booker |
| 5,782,840 | A | | 7/1998 | Nakao |
| 5,868,754 | A | | 2/1999 | Levine et al. |
| 6,348,056 | B1 | | 2/2002 | Bates et al. |
| 8,615,310 | B2 | | 12/2013 | Khairkhahan et al. |
| 9,126,032 | B2 | | 9/2015 | Khairkhahan et al. |
| 2003/0050663 | A1 | * | 3/2003 | Khachin ............. A61B 17/221 606/200 |
| 2006/0064114 | A1 | * | 3/2006 | Obitsu ................ A61B 17/221 606/113 |
| 2012/0004647 | A1 | | 1/2012 | Cowley |
| 2012/0046667 | A1 | | 2/2012 | Cherry et al. |
| 2012/0109149 | A1 | | 5/2012 | Bonner et al. |
| 2012/0172690 | A1 | | 7/2012 | Anderson et al. |
| 2013/0053921 | A1 | * | 2/2013 | Bonner ................ A61N 1/3756 607/36 |
| 2014/0180306 | A1 | | 6/2014 | Grubac et al. |
| 2014/0200462 | A1 | | 7/2014 | Stalker et al. |
| 2015/0051609 | A1 | | 2/2015 | Schmidt et al. |
| 2015/0051682 | A1 | * | 2/2015 | Schmidt ............. A61N 1/37205 607/127 |
| 2015/0094668 | A1 | | 4/2015 | Wood et al. |
| 2015/0273212 | A1 | | 10/2015 | Berthiaume et al. |

FOREIGN PATENT DOCUMENTS

| | | |
|---|---|---|
| EP | 3056157 A2 | 8/2016 |
| WO | 9406357 A1 | 3/1994 |
| WO | 2016090360 A1 | 6/2016 |

OTHER PUBLICATIONS

U.S. Appl. No. 15/234,023 entitled "Interventional Medical Systems and Catheters".
U.S. Appl. No. 14/812,224 entitled "Interventional Medical Systems, Catheters, and Methods".
U.S. Appl. No. 14/942,609 entitled "Interventional Medical Systems and Associated Methods".
U.S. Appl. No. 14/872,770 entitled "Interventional Medical Systems, Catheters, and Methods".
(PCT/US2017/051305) PCT Notification of Transmittal of the International Search Report and the Written Opinion of the International Searching Authority, dated Nov. 29, 2017, 15 pages.
First Office Action and Search Report, and translation thereof, from counterpart Chinese Application No. 201780069057.9, dated Dec. 28, 2020, 23 pp.

* cited by examiner

INTERVENTIONAL MEDICAL SYSTEMS AND RETRIEVAL TOOLS THEREOF

FIELD OF THE DISCLOSURE

The present disclosure pertains to interventional medical systems and tools thereof for retrieving a medical device from an implant site.

BACKGROUND

Figure 1:
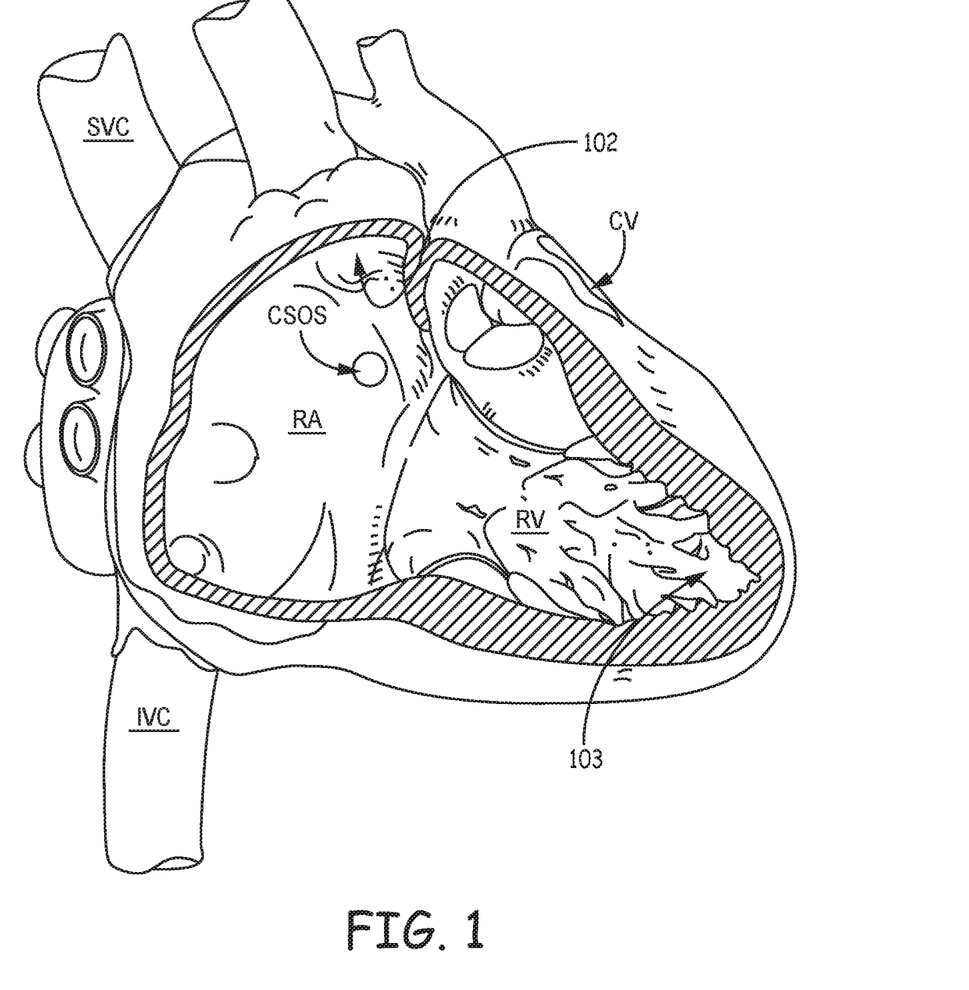
FIG. 1 is a schematic diagram showing potential implant sites for a relatively compact implantable medical device.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and are well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

Figure 2:
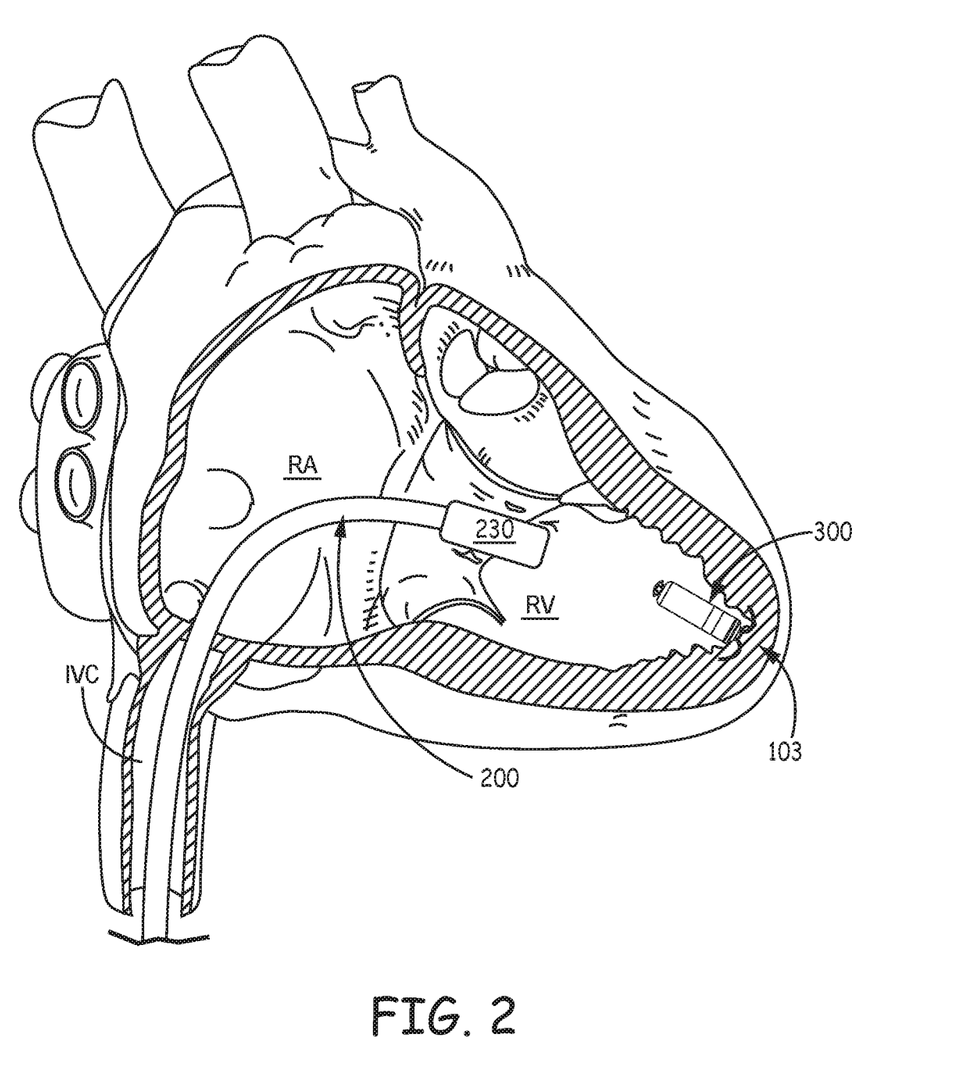
FIG. 2 is a schematic diagram showing an exemplary relatively compact implantable medical device having been delivered from a catheter to an implant site.

FIG. 2 shows an implantable medical device 300 having been implanted by an operator, for example, using a catheter 200 like a tool described in the commonly assigned United States Patent Application US 2015/0094668. The operator, having advanced catheter 200 into the right heart through the inferior vena cava IVC, for example, from a femoral vein access site, deploys device 300 from a receptacle defined by a sidewall 230 of a distal-most portion of catheter 200. In some cases, when it may be necessary to retrieve the implanted device, the operator can employ a snare tool, known in the art, in conjunction with catheter 200, but new and improved tools would increase the ease and efficiency of the retrieval.

SUMMARY

Embodiments of interventional medical systems disclosed herein include a retrieval tool operable with a catheter of the system for retrieving a medical device of the system from an implant site, wherein the device includes an attachment feature that forms an annular recess to be engaged by a lasso of the tool for snaring the device, and wherein a distal-most sidewall of the catheter defines a receptacle into which the snared device may be retrieved. In the disclosed embodiments, a guide of the tool includes a sidewall that defines a lumen in which the lasso extends and from which the lasso may be deployed, out from a distal opening thereof, to snare and retrieve the implanted device. The guide sidewall establishes a radial offset between the distal opening of the guide lumen, and the distal-most sidewall of the catheter, when the distal opening of the guide lumen is located in close proximity to a distal opening of the receptacle, wherein the radial offset is greater than a length of the annular recess formed by the device attachment feature. This radial offset can keep the annular recess of the snared device from 'hanging up', or catching on the distal-most sidewall of the catheter, at the distal opening of the receptacle, as an operator retrieves the snared device into the receptacle.

According to some embodiments, the sidewall of the retrieval tool guide tapers, preferably over a relatively short length, from a first outer diameter to a smaller, second outer diameter at the distal opening of the guide lumen, to establish the aforementioned radial offset, and the sidewall may be formed by a coiled member.

In some embodiments the guide may further include a rod that extends proximally from a proximal opening of the guide lumen and to which a first segment of the lasso may be fixedly attached. A second segment of the lasso, which extends from a distal end of the first segment and loops back alongside the first segment within the guide lumen, is moveable relative to the first segment to increase and decrease a length of the second segment that protrudes out from the distal opening of the guide lumen. In some embodiments, the tool further includes an elongate tube coupled to a proximal end of the lasso second segment, wherein the tube extends around the guide rod, being in sliding engagement therewith. Thus, the tube may be employed by the operator to move the second segment of the lasso when snaring the medical device.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 3:
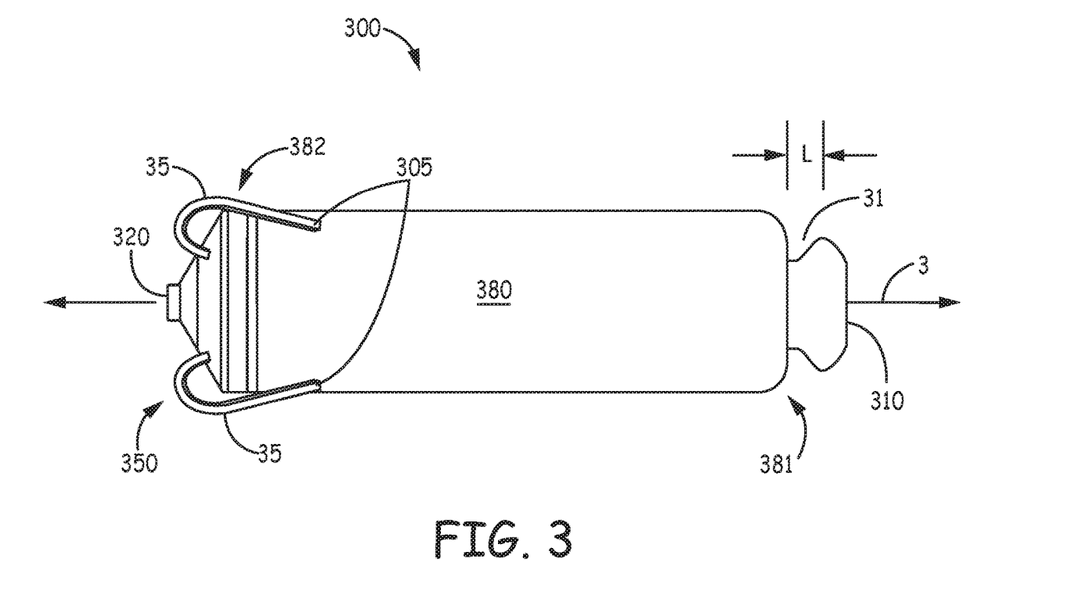
FIG. 3 is a plan view of the exemplary relatively compact implantable medical device, which may be part of an interventional medical system, according to some embodiments.

FIG. 3 is a plan view of exemplary relatively compact implantable medical device 300, which may be part of an interventional medical system, according to some embodiments. FIG. 3 illustrates device 300 including a hermetically sealed housing 380 extending from a proximal end 381 thereof to a distal end 382 thereof and along a longitudinal axis 3. Device 300 further includes an electrode 320 and a fixation member 350, both mounted in proximity to distal end 382 of housing 380, and an electronic controller (not shown), for example, a pulse generator and an associated power supply, contained in housing 380, wherein electrode 320 is electrically coupled to the controller via a hermetically sealed feedthrough assembly (not shown) such as is known in the art.

Housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. Device fixation member 350 is shown including a plurality of fingers 35 spaced apart from one another around a perimeter of device housing distal end 382. Although only two fingers 35 of fixation member 350 are shown in FIG. 3, fixation member 350 may include as many as eight fingers 35. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation member 350 may be mounted to distal end 382 of device housing 380, for example, in a manner similar to that described for a fixation component 102 in co-pending and commonly assigned United States Patent Application 2012/0172690.

FIG. 3 further illustrates device 300 including an attachment feature 310 joined to proximal end 381 of housing 380. Attachment feature 310 is shown forming an annular recess 31, which has a length L, where feature 310 is joined to housing proximal end 381. A looped portion of a retrieval tool may engage with recess 31 for snaring device 300 to retrieve device 300 from an implant site, as further described below, for example, when fingers 35 of device fixation member 350 are engaged with tissue at the implant site.

Figure 4:
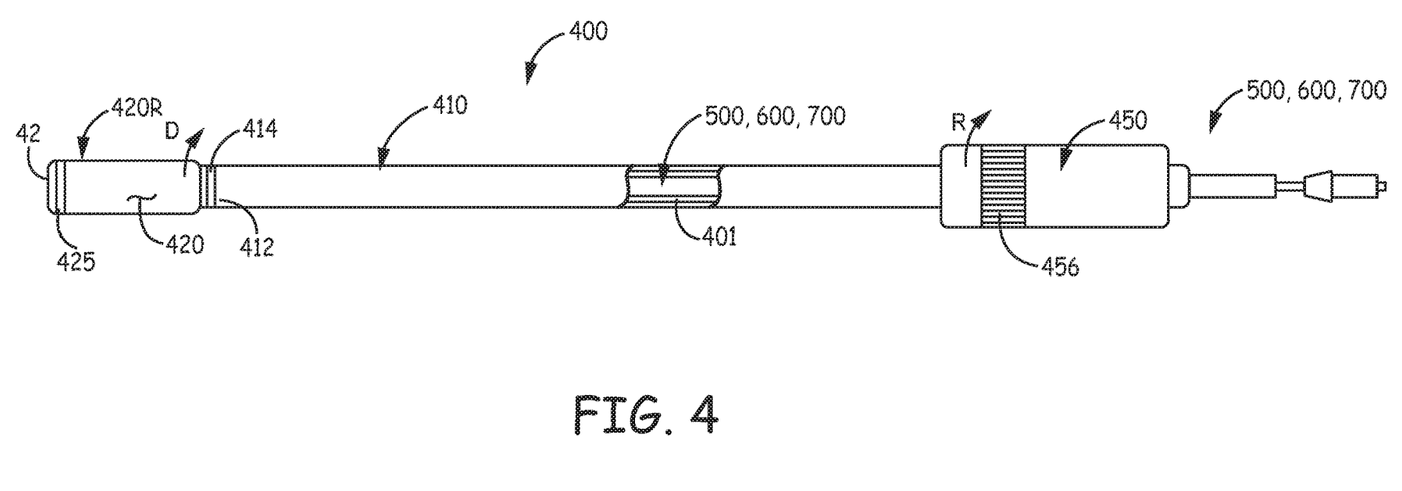
FIG. 4 is a plan view of an exemplary catheter and a retrieval tool in the interventional medical system, according to some embodiments.

FIG. 4 is a plan view of an exemplary catheter 400 of an interventional medical system, according to some embodiments, which may accommodate an one of retrieval tools 500, 600, 700 described below. FIG. 4 illustrates catheter 400 including an elongate shaft 410, a handle 450 terminating a proximal end of shaft 410, and a distal-most sidewall 420 being joined to a distal end 412 of shaft 410 and defining a receptacle 420R. An interior of receptacle 420R is sized to contain a medical device, such as device 300 of FIG. 3, wherein a distal opening 42 of the interior allows passage of device 300 therethrough. According to the illustrated embodiment, catheter shaft 410 includes an elongate lumen 401 in fluid communication with the interior of receptacle 420R, wherein lumen 401 and receptacle 420R accommodate, in sliding engagement therewith, any one of retrieval tools 500, 600, 700. It should be noted that catheter 400 may also be employed to deliver device 300 to the implant site.

According to an exemplary embodiment, catheter shaft 410, for example, extending over a length of approximately 100 cm, may be formed by a stainless steel braid-reinforced medical grade polymer of one or more appropriate grades of polyether block amide, which are arranged for decreasing stiffness from handle 450 to shaft distal end 412 (e.g., PEBAX® 3533, 6333, 4033, and 7233); and distal-most sidewall 420 may be formed from PEBAX® 7233 and include a radiopaque marker band 425 bonded thereto, for example, a polyamide material with a radiopaque filler, such as Tungsten-filled Vestamid®, or a Tungsten loaded PEBAX®. Shaft lumen 401 may have a diameter of approximately 0.154 inch (3.9 mm), and the interior of receptacle 420R may have a diameter of approximately 0.278 inch (7 mm). Catheter 400 may also have a deflection assembly integrated into shaft 410 and handle 450, which, with reference to FIG. 4, includes a deflection band 414 mounted around distal end 412 of shaft 410, an actuator 456 mounted to handle 450, and an elongate pull wire (not shown) extending along a length of shaft 410, being coupled at either end to band 414 and to actuator 456, according to any suitable construction known in the art. With further reference to FIG. 4, when an operator rotates actuator 456, per arrow R, the pull wire is moved to cause a deflection of receptacle 420R, per arrow D, which may help in navigating catheter 400 through a patient's venous system, and in positioning distal opening 42 of receptacle in proximity with implanted device 300. When distal opening 42 is thus positioned, the operator may advance retrieval tool 500, 600, 700 out from distal opening 42 to snare device 300.

Figure 5A:
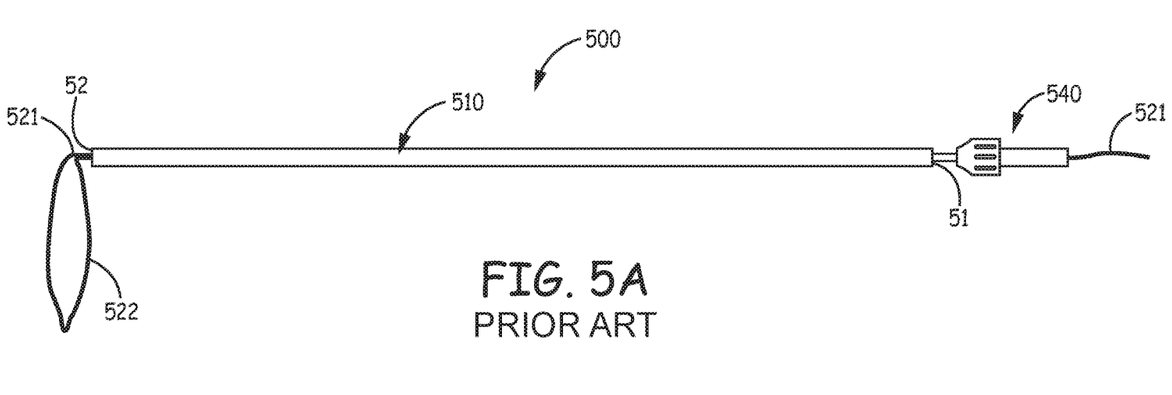
FIG. 5A is a plan view of an exemplary retrieval tool.
Figure 5B:
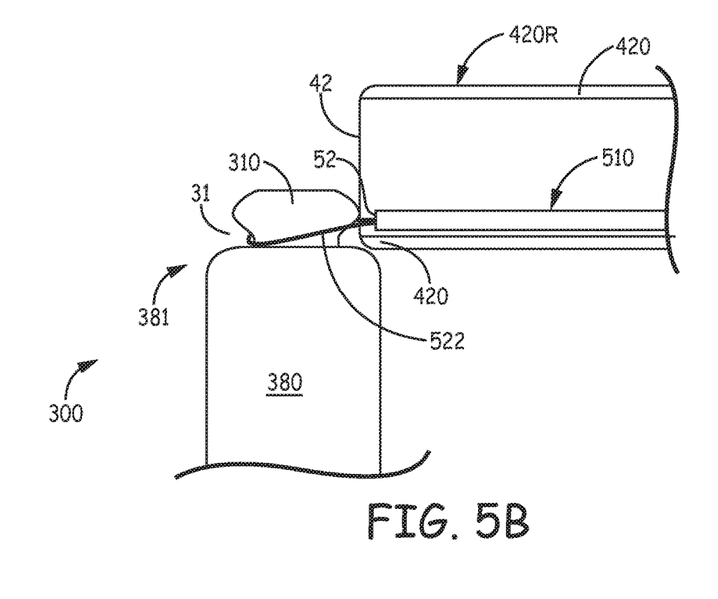
FIG. 5B is a schematic showing a catching of the medical device snared with the tool of FIG. 5A.

FIG. 5A is a plan view of retrieval tool 500, which is generally configured according to a prior art design, for example, like that disclosed in U.S. Pat. No. 5,171,233. FIG. 5A illustrates tool 500 including a snare wire 521 formed from a shape memory material, for example, a Nitinol wire, which extends within a sheath, or guide 510 of tool 500, and which is formed with a distal loop 522. Distal loop 522, which has a fixed perimeter length, is shown expanded, distal to a distal opening 52 of guide 510, and is configured to contract when pulled into guide 510. FIG. 5A further illustrates a grip tool 540 secured to a proximal end of snare wire 521, which protrudes out from a proximal opening 51 of guide 510. Grip tool 540 is configured to facilitate the operator's handling of wire 521, for example, in pulling loop 522 proximally into guide 510 after engaging loop 522 with annular recess 31 formed by device attachment feature 310, to snare device 300 as shown in the schematic of FIG. 5B. FIG. 5B illustrates snared device 300 'hanging up', or catching on distal-most sidewall 420 of catheter 400, at distal opening 42 of receptacle 420R when the operator retracts tool 500 relative to catheter 400 to retrieve the snared device 300 into receptacle 420R. Embodiments of the present invention, for example, exemplified by retrieval tool 700, described below in conjunction with FIGS. 7A-C, are configured to prevent such catching in retrieving implanted device 300.

Figure 6A:
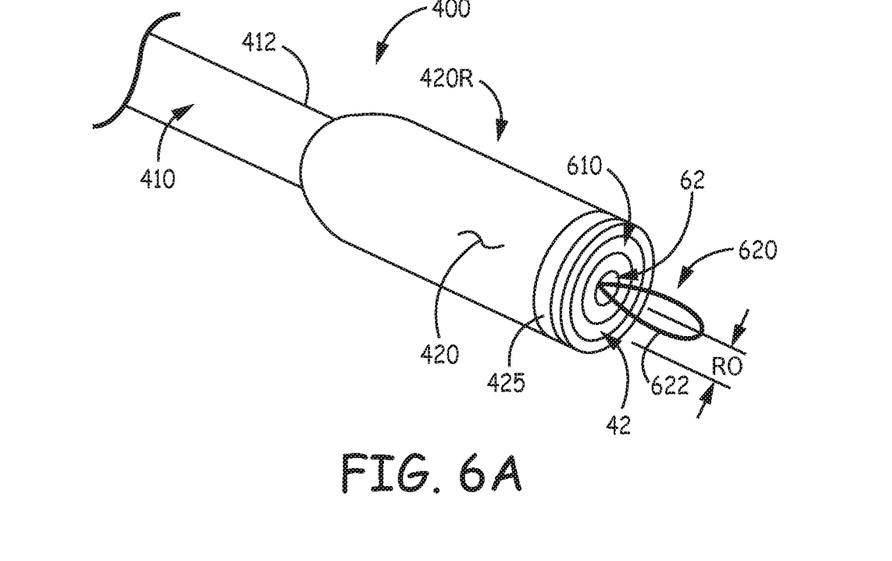
FIGS. 6A-B are schematics showing an advantageous retrieval tool feature for snaring the medical device, according to some embodiments of the present invention.
Figure 6B:
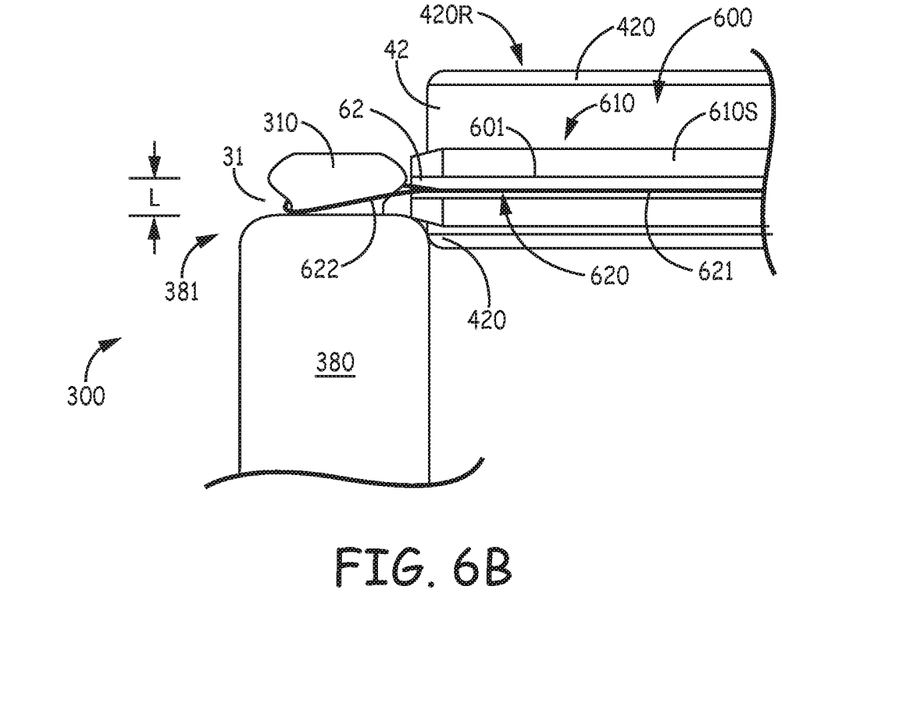

FIGS. 6A-B are schematics showing an advantageous retrieval tool feature for snaring medical device 300, according to embodiments of the present invention. FIGS. 6A-B illustrate retrieval tool 600 being loaded in sliding engagement within catheter 400, and including a guide 610 and a lasso 620, wherein a sidewall 610S of guide 610 defines an elongate lumen 601 of guide 610 in which a first segment 621 of lasso 620 extends. FIGS. 6A-B further illustrate a second segment 622 of lasso 620 protruding distally from a distal opening 62 of guide lumen 601, and being formed in a loop to snare device 300. With reference to FIG. 6A, guide sidewall 610S establishes a radial offset RO between distal opening 62 of guide lumen 601 and distal-most sidewall 420 of catheter when guide lumen distal opening 62 is located in close proximity to distal opening 42 of the interior of receptacle 420R. With reference to FIG. 6B, radial offset RO is greater than length L of annular recess 31, formed by device attachment feature 310, so that, when the operator retracts tool 600 to retrieve the snared device 301 into receptacle 420R, the above-described catching of device 300 on sidewall 420 is avoided.

Figure 7A:
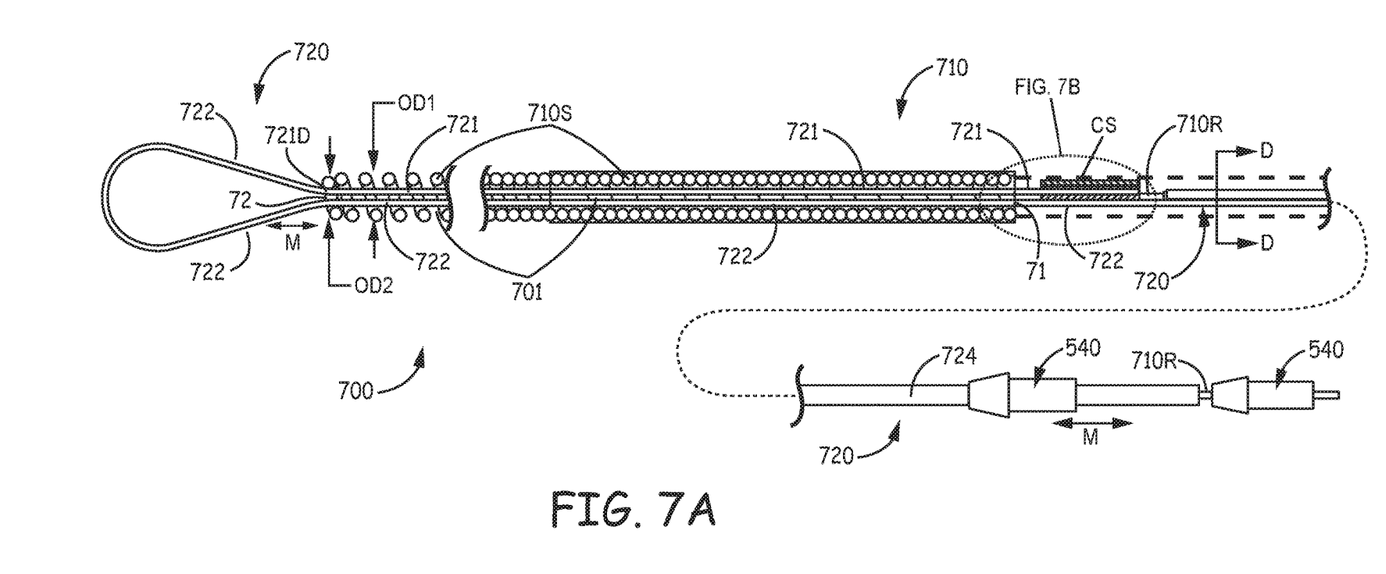
FIG. 7A is a plan view, including a longitudinal cross-section view, of an exemplary retrieval tool, according to some embodiments.
Figure 7B:
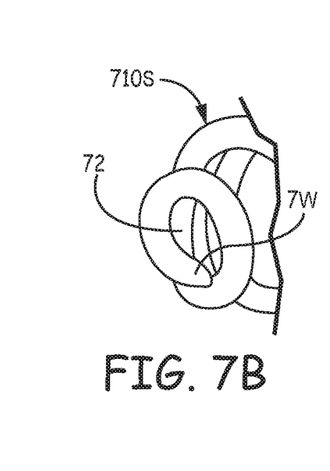
FIG. 7B is an enlarged perspective view of a portion of a guide sidewall of the tool of FIG. 7A, according to some embodiments.
Figure 7C:
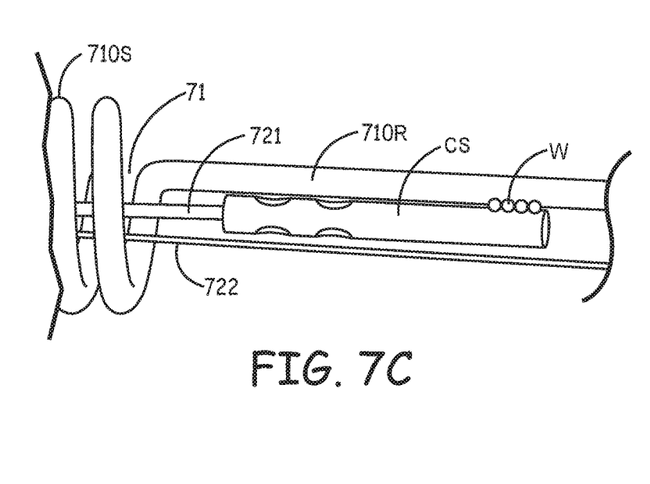
FIG. 7C is an enlarged detail view of another portion of the tool of FIG. 7A, according to some embodiments.

FIG. 7A is a plan view, including a longitudinal cross-section view, of retrieval tool 700, according to some embodiments. As described above in conjunction with FIG. 4, catheter 400 is configured to receive retrieval tool 700 in sliding engagement therein. FIG. 7A illustrates tool 700 including a guide 710 and a lasso 720, wherein a sidewall 710S of guide 710 defines a longitudinally extending lumen 701 in which lasso 720 extends. FIG. 7A further illustrates lasso 720 including a first segment 721 and a second segment 722 that extends from a distal end 721D of first segment 721, protruding distally from a distal opening 72 of guide lumen 701, and looping back alongside first segment 721 within guide lumen 701. According to the illustrated embodiment, lasso first segment 721 is fixedly attached to guide 710, for example, as described below in conjunction with FIG. 7C, and lasso second segment 722, which is configured to engage with annular recess 31 of device 300 (FIG. 3), is movable per arrow M, relative to first segment 721, to increase and decrease a length of second segment 722 that protrudes from distal opening 72. Thus, in contrast to the fixed perimeter length of loop 522 of the prior art tool 500, the operator can increase and decrease a perimeter length of the loop formed by second segment 722, which allows for a variety of expanded loop sizes. A means for moving lasso second segment 722 is described below. First and second segments 721, 722 of lasso 720 may be integrally formed from a shape memory alloy wire, for example, a Nitinol wire having a diameter of about 0.01 inch. In some preferred embodiments, to facilitate fluoroscopic visualization, the portion of lasso second segment 722 that can protrude distally from distal opening 72 of guide lumen 701, to form the loop for snaring device 300, is wrapped with a relatively fine (e.g., 0.0025 inch diameter) radiopaque wire, for example, a coiled Tantalum wire. The wrapped/coiled wire may be overlaid with a polymer tubing and held in place by stoppers mounted about lasso 720 at either end of the wrapped/coiled wire, wherein the overlaid tubing and each of the stoppers may be formed by a heat shrink tubing, such as a polyester medical heat shrink tubing supplied by Vention Medical.

With further reference to FIG. 7A, guide sidewall 710S tapers from a first outer diameter OD1 to a smaller, second outer diameter OD2 at distal opening 72 of guide lumen 701, so that guide sidewall 710S establishes a radial offset between distal opening 72 and distal-most sidewall 420 of catheter 400, when distal opening 72 is located in close proximity to distal opening 42 of catheter receptacle 420R, for example, like radial offset RO shown in FIG. 6A. A ratio of second diameter OD2 to first diameter OD1 is preferably no greater than about 60%, and the radial offset established by the tapering is greater than length L of annular recess 31 formed by device attachment feature 310 (FIG. 3). Furthermore, a length of the taper is preferably relatively short, for example, no greater than about 0.08 inch. According to an exemplary embodiment, first outer diameter OD1 is approximately 0.13 inch, and second outer diameter OD2 is approximately 0.08 inch. Thus, tool 700 is configured to prevent device 300, when snared with lasso second segment 722, from catching on distal-most sidewall 420 of catheter 400, when the operator retracts tool 700 to retrieve device into receptacle 420R of catheter 400, in a similar fashion to that shown in the schematic of FIG. 6B.

FIG. 7A further illustrates guide sidewall 710S being formed by a coiled member, for example, a medical grade stainless steel wire that has a diameter of about 0.02 inch, according to some embodiments. When lasso second segment 722, engaged with annular recess 31, is tightened by the operator around device attachment feature 310 to snare device 300, the implanted device 300 is oriented generally orthogonal to a length of receptacle 420R, for example, as shown in FIG. 6A, so that the flexibility of guide sidewall 710S, for example, imparted by the coil construction, allows retrieval tool guide 710, in proximity to distal opening 72 thereof, to bend as the operator retracts device 300 into receptacle 420R of catheter 400. According to some embodiments, and with reference to FIG. 7B, which is an enlarged perspective view of guide sidewall 710S, at distal opening 72 of guide lumen 701, distal opening 72 is defined by a distal-most turn of the coiled member (second outer diameter OD2) where a weld 7W between a distal end of the turn and a proximal end of the turn forms an eyelet.

FIG. 7A in conjunction with FIG. 7C, which is an enlarged detail view of a portion of the tool that is circled in FIG. 7A, illustrate guide 710 also including a rod 710R that extends proximally from a proximal opening 71 of guide lumen 701, preferably in a relatively straight line. According to the illustrated embodiment, lasso first segment 721 is fixedly attached to guide 710 at guide rod 710R, for example, by a sleeve CS crimped around first segment 721 and a weld W between crimped sleeve CS and guide rod 710R. Of course, alternative suitable means are known to those skilled in the art for fixedly attaching lasso first segment 721 to guide 720, and may be employed in some alternate embodiments. In an exemplary embodiment, guide rod 710R and guide sidewall 710S are integrally formed, for example, from the same medical grade stainless steel wire.

Figure 7D:
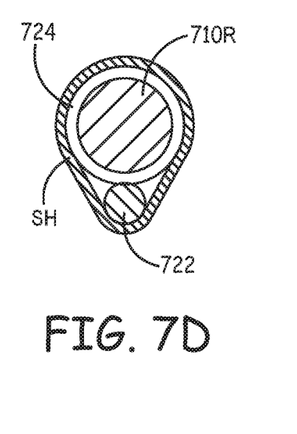
FIG. 7D is a cross-section view through section line C-C of FIG. 7A, according to some embodiments.

FIGS. 7A and 7C further illustrate a proximal end of lasso second segment 722 extending proximally from guide lumen proximal opening 71 and alongside the attachment of lasso first segment 721 to guide rod 710R. FIG. 7A in conjunction with FIG. 7D, which is a cross-section view through section line D-D of FIG. 7A, illustrate lasso 720 also including an elongate tube 724 coupled to the proximal end of second segment 722 and extending around guide rod 710R, being in sliding engagement therewith, wherein tube 724 is coupled to lasso second segment 722 by means of an overlying layer of a medical grade heat shrink tubing SH, such as a polyester heat shrink tubing. Tube 724 may have an inner diameter of about 0.023 inch with a wall thickness of about 0.003 inch, and be formed from a medical grade polyimide, such as that supplied by Vention Medical. According to the illustrated embodiment, the operator may grasp and slide tube 724 back and forth along guide rod 710R to move lasso second segment 722 per arrow M, for example, when snaring medical device 300. With further reference to FIG. 7A, one grip tool 540 is shown secured to a proximal end of guide rod 710R and another grip tool 540 secured to tube 724 so that the operator may more easily grip guide rod 710R in one hand while gripping and moving tube 724 with the other hand. In some embodiments, a coil (shown with dashed lines) may extend around the attachment between lasso first segment 721 and guide rod 710R and around a portion of the proximal end of lasso second segment 722 and tube 724, where heat shrink tubing SH couples segment 722 and tube 724 together, for example, to prevent lasso second segment 722 from buckling as the operator moves second segment 722 in the distal direction. In some embodiments, the coil may be 'screwed' together with guide sidewall 710S in proximity to guide lumen proximal opening 71, and a polymer overlay 712, such as medical grade polyester heat shrink tubing, may be included to secure the coil together with guide sidewall 710S. According to an exemplary embodiment, an overall length of guide sidewall 710S may be in a range from about 3 inches to about 10 inches, wherein the longer length may include the coil as an extension of sidewall 710S.

Figure 8:
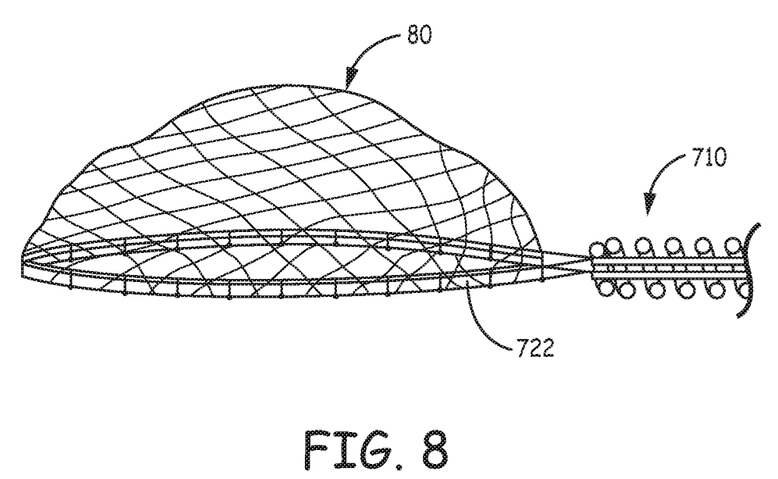
FIG. 8 is a plan view of an optional feature included in some embodiments.

FIG. 8 is a plan view of an optional net 80 that may be secured to lasso second segment 722, according to some embodiments. Net 80 may be generally constructed according to the disclosure of U.S. Pat. No. 5,782,840, for example, from a web and a plurality of sliding connecting strands spaced apart about a perimeter of the web and being joined to lasso second segment 722. The web and strands may be formed from a medical grade polymer, for example, polyethylene, polyester, or nylon. Net 80 may provide a kind of stop that keeps the operator from initially positioning lasso second segment 722 around device housing 380, distal to annular recess 31 formed by device attachment feature 310 (FIG. 3), which may facilitate a quicker snaring of device 300 by engagement of lasso second segment 722 with recess 31.

In the foregoing detailed description, the invention has been described with reference to specific embodiments. However, it may be appreciated that various modifications and changes can be made without departing from the scope of the invention as set forth in the appended claims.

We claim:

1. An interventional medical system comprising an implantable medical device, a catheter, and a retrieval tool;
the implantable medical device comprising a hermetically sealed housing extending along a longitudinal axis between a proximal end thereof and a distal end thereof, and an attachment feature joined to the proximal end of the housing, the attachment feature forming an annular recess where the feature is joined to the housing proximal end;
the catheter comprising an elongate shaft and a distal-most catheter sidewall joined to a distal end of the shaft, the distal-most catheter sidewall defining a receptacle extending along a first central axis and sized to contain an entirety of the implantable medical device therein, the shaft including a longitudinally extending lumen in fluid communication with an interior of the receptacle, the interior of the receptacle having a distal opening sized to receive passage of the implantable medical device therethrough, and the shaft lumen and the receptacle being sized to receive the retrieval tool in sliding engagement therein; and
the retrieval tool comprising:
an elongate guide comprising:
a guide sidewall defining a longitudinally extending guide lumen of the elongate guide extending along a second central axis, the guide lumen extending from a proximal opening thereof to a distal opening thereof; and
a rod extending proximally from the proximal opening of the guide lumen, and
wherein the guide sidewall tapers from a first outer diameter to a smaller, second outer diameter at the distal opening to establish, when the second central axis is radially offset from the first central axis, the distal opening of the guide lumen is axially proximate the distal opening of the receptacle and the guide sidewall is directly adjacent the distal-most catheter sidewall, a radial offset between the distal opening of the guide lumen and the distal-most catheter sidewall; and
a lasso comprising:
a first segment extending within the guide lumen and being fixedly attached to the elongate guide, the first segment having a distal end located in close proximity to the distal opening of the guide lumen;
a second segment extending from the distal end of the first segment and looping back alongside the first segment within the guide lumen, the second segment being moveable relative to the first segment to increase and decrease a length of the second segment that protrudes distally from the distal opening of the guide lumen, and the second segment being configured to engage with the annular recess formed by the implantable medical device attachment feature; and
an elongate tube coupled to a proximal end of the second segment of the lasso by an overlying layer of heat shrink tubing, wherein the elongate tube extends around the rod of the elongate guide, and wherein the elongate tube is in sliding engagement with the rod;
wherein the radial offset established by the guide sidewall is greater than a length of the annular recess formed by the attachment feature of the implantable medical device.

2. The system of claim 1, wherein the guide sidewall is formed by a coiled member.

3. The system of claim 1, wherein the first segment of the lasso is fixedly attached to the rod.

4. The system of claim 1, wherein a length along which the guide sidewall tapers is not more than about 0.08 inch.

5. The system of claim 1, wherein the retrieval tool further comprises a net, the net being coupled to a portion of the second segment of the lasso, the portion of the second segment being adjacent the distal end of the first segment of the lasso.

6. The system of claim 1, wherein the rod is integrally formed with the guide sidewall.

7. A tool for retrieving, in conjunction with a catheter, an implantable medical device from an implant site and into a receptacle of the catheter, the catheter comprising a distal-most catheter sidewall and the receptacle extending along a first central axis, the implantable medical device comprising a hermetically sealed housing extending along a longitudinal axis between a proximal end thereof and a distal end thereof, and an attachment feature joined to the proximal end of the housing, the attachment feature forming an annular recess where the attachment feature is joined to the proximal end of the housing, the tool being sized to fit in sliding engagement within the receptacle of the catheter, and the tool comprising:
an elongate guide comprising:
a guide sidewall defining a longitudinally extending guide lumen of the elongate guide extending along a second central axis, the guide lumen extending from a proximal opening thereof to a distal opening thereof, and the guide sidewall tapering from a first outer diameter to a smaller, second outer diameter at the distal opening of the guide lumen, the tapering extending over a length no greater than about 0.08 inch, and a ratio of the smaller, second outer diameter to the first outer diameter being no greater than about 60%;

a rod extending proximally from the proximal opening of the guide lumen, wherein the tapering of the guide sidewall establishes, when the second central axis is radially offset from the first central axis, the distal opening of the guide lumen is axially proximate the distal opening of the receptacle and the guide sidewall is directly adjacent the distal-most catheter sidewall, a radial offset between the distal opening of the guide lumen and the distal-most catheter sidewall; and a lasso comprising:
  a first segment extending within the guide lumen and being fixedly attached to the elongate guide, the first segment having a distal end located in close proximity to the distal opening of the guide lumen;
  a second segment extending from the distal end of the first segment and looping back alongside the first segment within the guide lumen, the second segment being moveable relative to the first segment to increase and decrease a length of the second segment that protrudes distally from the distal opening of the guide lumen, and the second segment being configured to engage with the annular recess formed by the attachment feature of the implantable medical device; and
  an elongate tube coupled to a proximal end of the second segment of the lasso by an overlying layer of heat shrink tubing, wherein the elongate tube extends around the rod of the elongate guide, and wherein the elongate tube is in sliding engagement with the rod.

8. The tool of claim 7, wherein the guide sidewall is flexible in proximity to the distal opening of the guide lumen.

9. The tool of claim 7, wherein the guide sidewall is formed by a coiled member.

10. The tool of claim 7, wherein the first segment of the lasso is fixedly attached to the rod.

11. The tool of claim 7, further comprising a net, the net being coupled to a portion of the second segment of the lasso, the portion of the second segment being adjacent the distal end of the first segment of the lasso.

12. The tool of claim 7, wherein the rod is integrally formed with the guide sidewall.

13. A tool for retrieving, in conjunction with a catheter, an implantable medical device from an implant site and into a receptacle of the catheter, the catheter comprising a distal-most catheter sidewall and the receptacle extending along a first central axis, the implantable medical device comprising a hermetically sealed housing extending along a longitudinal axis between a proximal end thereof and a distal end thereof, and an attachment feature joined to the proximal end of the housing, the attachment feature forming an annular recess where the attachment feature is joined to the proximal end of the housing, the tool being sized to fit in sliding engagement within the receptacle of the catheter, and the tool comprising:

an elongate guide comprising a relatively straight rod portion and a coiled portion, the coiled portion forming a guide sidewall, the guide sidewall defining a longitudinally extending guide lumen of the elongate guide extending along a second central axis, the guide lumen extending from a proximal opening thereof to a distal opening thereof, the rod portion being integrally formed with the coiled portion and extending proximally from the proximal opening of the guide lumen, and the guide sidewall tapering from a first outer diameter to a smaller, second outer diameter at the distal opening of the guide lumen, wherein the tapering of the guide sidewall establishes, when the second central axis is radially offset from first central axis, the distal opening of the guide lumen is axially proximate a distal opening of the receptacle and the guide sidewall is directly adjacent the distal-most catheter sidewall, a radial offset between the distal opening of the guide lumen and the distal-most catheter sidewall; and a lasso comprising:
  a first segment extending within the guide lumen and being fixedly attached to the rod portion of the elongate guide, the first segment having a distal end located in close proximity to the distal opening of the guide lumen;
  a second segment extending from the distal end of the first segment and looping back alongside the first segment within the guide lumen, the second segment further extending proximally from the proximal opening of the guide lumen and alongside the rod portion of the elongate guide, the second segment being moveable relative to the first segment to increase and decrease a length of the second segment that protrudes distally from the distal opening of the guide lumen, and the second segment being configured to engage with the annular recess formed by the attachment feature of the implantable medical device; and
  an elongate tube coupled to a proximal end of the second segment of the lasso by an overlying layer of heat shrink tubing, wherein the elongate tube extends around the rod portion of the elongate guide, and wherein the elongate tube is in sliding engagement with the rod portion.

14. The tool of claim 13, wherein the coiled portion of the elongate guide has a close wound pitch along a first length corresponding to the first outer diameter, and a space wound pitch along a distal-most, second length corresponding to the tapering from the first outer diameter to the smaller, second outer diameter.

15. The tool of claim 13, wherein the tapering of the guide sidewall extends over a length no greater than about 0.08 inch, and a ratio of the smaller, second outer diameter to the first outer diameter is no greater than about 60%.

16. The tool of claim 13, further comprising a net, the net being coupled to a portion of the second segment of the lasso, the portion being adjacent the distal end of the first segment of the lasso.

* * * * *